US007154985B2

United States Patent
Dobbs et al.

(10) Patent No.: US 7,154,985 B2
(45) Date of Patent: Dec. 26, 2006

(54) METHOD AND SYSTEM FOR SIMULATING X-RAY IMAGES

(75) Inventors: Andrew Bruno Dobbs, Vallåkra (SE); Niels Husted Kjær, Hedehusene (DK)

(73) Assignee: Medical Insight A/S, Hedehusene (DK)

( * ) Notice: Subject to any disclaimer, the term of this patent is extended or adjusted under 35 U.S.C. 154(b) by 61 days.

(21) Appl. No.: 10/844,506

(22) Filed: May 13, 2004

(65) Prior Publication Data
US 2004/0228453 A1    Nov. 18, 2004

(51) Int. Cl.
*A61B 6/03* (2006.01)
(52) U.S. Cl. .......................................... 378/4
(58) Field of Classification Search ................... 378/4, 378/8, 15, 19, 901
See application file for complete search history.

(56) References Cited

U.S. PATENT DOCUMENTS 5,297,037 A    3/1994    Ifuku
2002/0191814 A1 *  12/2002  Ellis et al. .................. 382/103

FOREIGN PATENT DOCUMENTS

EP    0 247 449 A    12/1987

OTHER PUBLICATIONS

Theo Van Walsum, et al., "CT-based Simulation of Fluoroscopy and DSA for Endovascular Surgery Training", CVRMED-MRCAS '97, First Joint Conference, Computer Vision, Virtual Reality and Robotics in Medicine and Medical Robotics and Computer-Assisted Surgery Proceedings, Mar. 19-22, 1997, pp. 273-282.
Stephane Cotin, et al., "Real-Time PC based X-ray Simulation for Interventional Radiology Training", Manivannan Muniyandi, Laboratory for Human and Machine Haptics, Massachusetts Institute of Technology, Feb. 28, 2003, 7 pages.
European Search Report.

* cited by examiner

*Primary Examiner*—Edward J. Glick
*Assistant Examiner*—Chih-Cheng Glen Kao
(74) *Attorney, Agent, or Firm*—Harness, Dickey & Pierce, P.L.C.

(57) ABSTRACT

The invention relates to simulating 2D X-ray images from 3D CT data. A user can access a repository of CT data of a patient's anatomy 2 by using a computer network system. The CT data has been obtained by a CT scanning of the patient 1. Firstly, the user retrieves the CT image data 3 and a 3D image is generated 4. Secondly, the user may orient the CT image in any orientation desirable with respect to a virtual X-ray source and a virtual image plane. And thirdly, a 2D X-ray image is simulated 6 from the chosen viewpoint and shown to the user.

6 Claims, 5 Drawing Sheets

METHOD AND SYSTEM FOR SIMULATING X-RAY IMAGES

FIELD OF THE INVENTION

The present invention relates to transforming 3D image data to 2D image data and in particular to simulating 2D X-ray images from CT data.

BACKGROUND OF THE INVENTION

Computed Tomography (CT) scanning of patient anatomy is used by radiologists for medical diagnosis. In CT scanning of a patient, a 3D (or volume) image is generated by means of an X-ray source which is rapidly rotated around the patient. A large quantity of images is obtained resulting in slices of the scanned area, which is electronically reassembled to constitute a 3D image of the scanned area. The CT scanning is a measurement of the amount of X-rays absorbed in the specific volume elements constituting the 3D image, and each volume element represents the density of the tissue comprised in the volume element.

The CT image is a 3D counterpart to the traditional 2D X-ray image. In order to obtain a 2D X-ray image, an X-ray source is mounted in a fixed position, and a patient is located and oriented in-between the X-ray source and a detecting screen. In this method a projection of the tissue density along the ray path is acquired.

If a medical diagnosis on the background of CT scanning necessitate surgery, a surgeon nearly always requests medical images in the operating theater that display the particular medical problem. In some instances, the original CT data of interest is printed to film, in the form of cross-sectional slices through the patient anatomy and these films are provided to the surgeon. In many other instances, however, the patient is sent to an X-ray facility for acquiring 2D X-ray images in addition to the CT images. The request for X-ray images is accompanied with a precisely specified patient position for the X-ray imaging procedure. Such 2D X-ray projection images are often requested by the surgeons because the slice images from CT data are frequently considered as not providing sufficient information, or the number of slice images is too large for use in an operation situation. Sending a patient to an X-ray facility for obtaining X-ray images is expensive, it takes time and it exposes the patient to additional X-ray radiation.

Furthermore, the positioning of a patient in an X-ray apparatus to obtain an optimal X-ray image is a skill that technicians must learn. Training is often done on-the-job, which sometimes requires re-acquiring X-ray images when the original images do not show the anatomy of interest in the correct way. Obtaining optimal X-ray images may be difficult due to organs shadowing the area of interest as well as a proper and precise positioning of the X-ray source and the detector plate.

To avoid exposing dental students to X-ray radiation during training of obtaining X-ray images of teeth, Umea University has built a virtual training system. The virtual training system comprises a tooth model acquired from a CT scanning. An X-ray image plate may be positioned and the virtual model may be oriented, and an X-ray image of the teeth is simulated.

DESCRIPTION OF THE INVENTION

It is an object of the present invention to facilitate access to 2D X-ray images of a patient under medical treatment who has undergone CT scanning. Accordingly there is provided, in a first aspect, a method of generating a simulated 2D X-ray image from CT data of a patient's anatomy, said method comprising the steps of:

CT scanning the patient to generate corresponding CT data at a first time instance;

storing the CT data in a data repository;

retrieving the CT data at a second time instance after the first time instance;

generating a 3D CT image of the anatomy from the CT data; and positioning a virtual X-ray source relative to a virtual image plane to generate the corresponding 2D simulated X-ray image, whereby the simulated X-ray image may be generated from an unrestricted viewpoint.

A patient is CT scanned and the data is stored in a data repository. The repository of patient CT data may be accessible to a user through a computer network. For example, the CT data may be stored on a computer-based system, such as a client-server computer network system. The server may be a central computer, or a central cluster of computers, and the CT data may be stored on the server or on a computer to which the server is connected. The client may be any type of client, e.g. a thin client, a PC, a tablet PC, a workstation, a laptop computer, a mobile hand held device, such as a digital personal assistant (PDA) or a mobile phone, or any other type of client. The user may be a medically trained person such as a clinician or a surgeon.

The present invention is, however, not limited to implementation on a client-server type system. It may be implemented on any type of system, including a workstation or a PC, or as a program implemented in connection with the Internet.

The patient is scanned at a first time instance. The CT data may after this time instance be retrieved at a second time instance. The second time instance may be any time instance after the first time instance, e.g. it may be during the preparations of an operation, or it may be during an operation. While actual X-ray images may be produced before the operation, it is impossible to obtain actual X-ray images during an operation. It is an advantage of the present invention that a simulated X-ray image may be obtained at any time instance after a patient has undergone CT scanning, including a time instance during an operation.

The CT image of a patient is acquired from a repository of patient CT data, for example by using a software application adapted to visualize CT data, i.e. adapted to generate a 3D image from the CT data. The software application is capable of orienting the 3D image with respect to a viewpoint and a virtual image plane, i.e. rotating the CT image. The application may, however, also be capable of other types of manipulation, such as zooming, cutting an area, etc. Positioning the virtual X-ray source relative to a virtual image plane corresponds to the positioning of the actual X-ray source in an X-ray facility. Likewise, the position of the virtual image plane corresponds to the position of the detector plane in an X-ray facility, and the virtual image plane may be viewed upon as a virtual X-ray detector.

The simulated X-ray image may be generated from a variable and unrestricted viewpoint. That is, the virtual X-ray source may be positioned independently with respect to the CT object. X-ray images may even be generated from a viewpoint, which is not possible in a real X-apparatus. In a real X-ray apparatus a number of viewpoints are not possible, because it is not possible to orient the patient in the required way.

A 2D X-ray image may be generated in any given orientation of the 3D CT image with respect to the virtual image plane.

The simulated X-ray images can be generated for any patient who has undergone CT scanning. After the patient has been scanned, the data may be made available by storing the data on a computer system that may be accessed by a user. For example, the user may be a surgeon who makes a diagnosis, plans a surgical operation, or a surgeon who needs further insight during an operation.

The simulated X-ray image may be simulated using parallel propagating X-rays, so that the X-ray image is simulated free of parallax distortion, i.e. an ideal X-ray image may be simulated. Alternatively the simulated X-ray image may be simulated using divergent X-rays, so that the X-ray image is simulated with parallax distortion as in actual X-ray images.

The CT data of patient anatomy may preferentially be based on data that conforms to the Digital Imaging and Communications in Medicine standard (DICOM standard) implemented on Picture Archiving and Communications Systems (PACS systems). Use of actual CT patient data in the DICOM format within a PACS system is an advantage since this enables to directly incorporate access to simulated X-ray images in the imaging workflow in a hospital.

The simulation algorithms may be texture based and adapted with special accumulation, color, and opacity buffers in a manner that Beer's law is approximated regarding the transmission and scattering of photons through physical media.

The simulation algorithms may work directly with volume CT data in the DICOM format. This is an advantage since simulated X-ray images may be provided without any preprocessing steps, such as segmenting of data. Techniques that rely on segmented data are more likely to be prone to errors.

Additionally, the disclosed method may be used for training of X-ray technicians via a computer system that allows the positioning of virtual patient anatomies based on CT data sets, and produces virtual X-ray images corresponding to the anatomy position and other imaging parameters. Such a system allows for a complete and realistic training.

According to a second aspect of the invention, a system for generating a simulated 2D X-ray image from CT data of a patient's anatomy is provided, the system comprising:
 a first device and a at least second device, where the first device and at least second device are interconnected in a computer network,
  where the first device stores CT data of the patient's anatomy, and
  where the at least second device comprises visualization means as well as inputting means capable of accepting request actions, wherein the patient CT data can be accessed from the at least second device, so that a 3D CT image of a patient, and subsequently the simulated 2D X-ray image can be visualized on the visualization means comprised in the at least second device.

The first device may be a server and the at least second device a client, interconnected in a client-server computer network system. The CT data may be stored on the first device, or on a device to which the server is connected by means of a computer network connection. The at least second device comprises visualization means, such as a screen on which data may be visualized both as 3D visualization and 2D visualization. The at least second device also comprises inputting means, such as a keyboard and a computer mouse, so that request actions, such as keystrokes, mouse movement, mouse clicking, etc. may be registered by the at least second device.

BRIEF DESCRIPTION OF THE DRAWINGS

Embodiments of the invention will now be described in details with reference to the drawings in which.

DETAILED DESCRIPTION OF THE INVENTION

The present invention provides a method and system for simulating a 2D X-ray image from CT data of a patient's anatomy.

Figure 1:
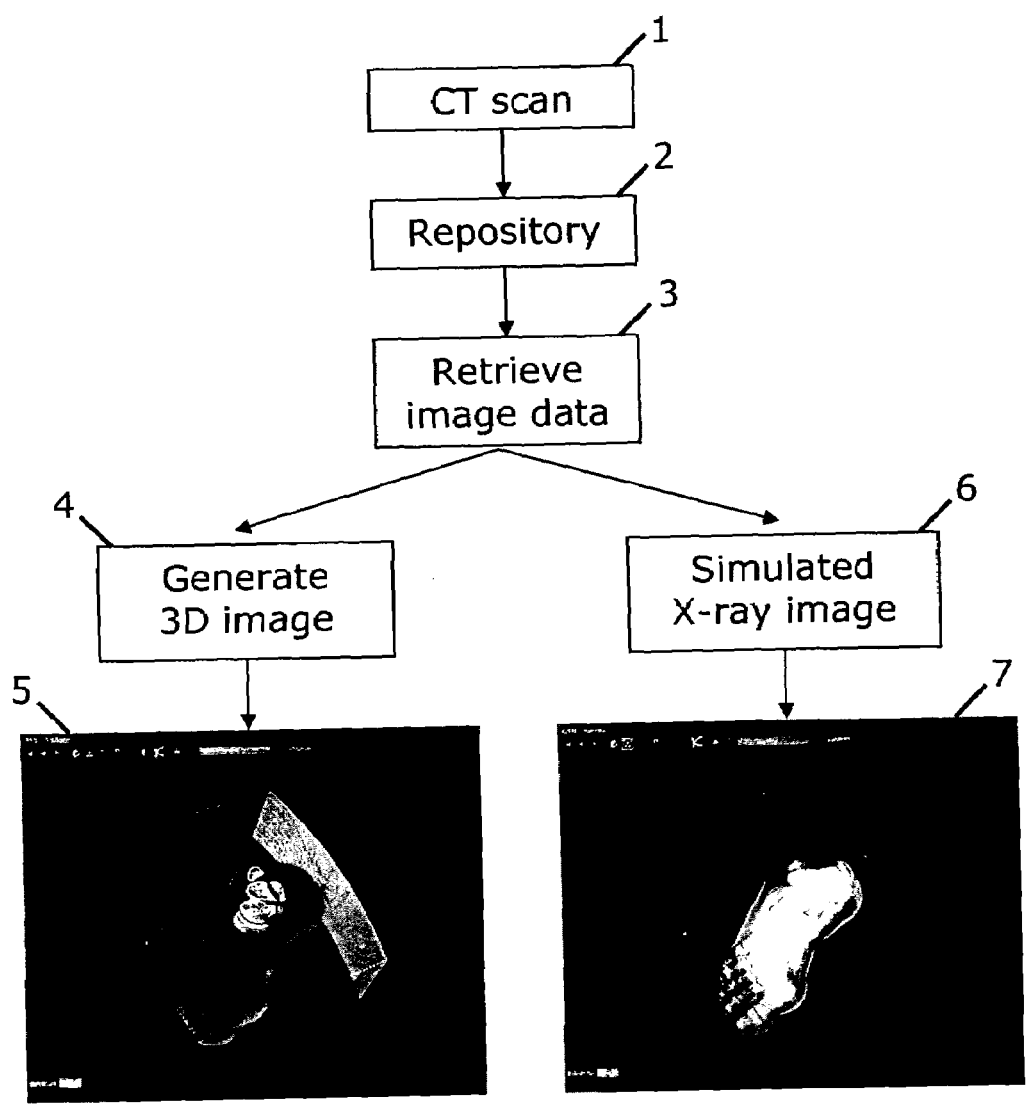
FIG. 1 illustrates the relationship between the 3D CT image and the simulated X-ray image.

In FIG. 1 a block diagram is showing how a CT data may be used either for 3D reconstruction of the CT data, or for simulating X-ray images. A patient is first CT scanned 1, after which the data is made accessible, via e.g. a computer network, by storing the CT data in a data repository 2. The data repository may be a hard disk or any other type of storage medium to which there may be gained access, e.g. via a computer network. The CT data may be retrieved 3 from the repository at any time instance after the data has been stored in the repository 2. A 3D CT image 4 can be generated from the CT data by using a data application such as a program adapted to generate 3D images. A screenshot 5 showing a 3D CT image is presented. The screenshot 5 shows a foot in a specific orientation as well a plate on which the foot was supported during the CT scanning. A 2D X-ray image is simulated 6 from the CT data. A screenshot 7 of the simulated X-ray image is presented, the support plate is naturally also present in the simulated image. The simulated X-ray image is generated in the plane coincident with the image plane of the screenshot. The 2D simulated X-ray image is generated as an alternative to an actual X-ray image. Obtaining an actual X-ray image requires sending the patient to an X-ray facility.

Figure 2:
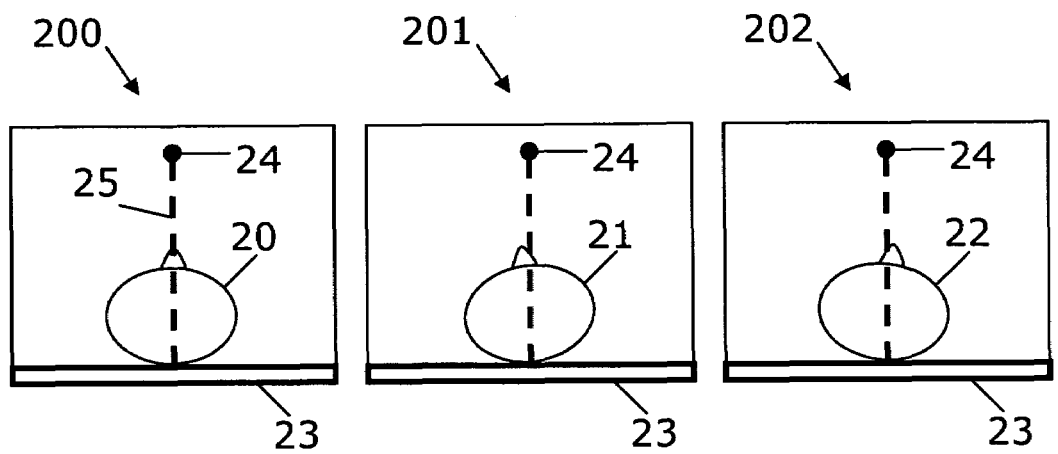
FIG. 2 illustrates the orientation of the 3D CT image relative to a viewpoint and a virtual image plane.

The 3D CT image may be orientated with respect to a position of the virtual X-ray source, i.e. a viewpoint, and a virtual image plane, this is illustrated in FIG. 2. The 3D CT image 20 may be rotated until a desired orientation is obtained, here exemplified by a schematic head viewed in a cross-sectional view 200. The orientation of the CT image 20 is relative to a virtual X-ray source 24, i.e. the X-ray source used in the simulation of the 2D X-ray image. The virtual X-ray source 24 is in a preferred embodiment positioned on a surface normal 25 to the virtual image plane 23. But the virtual X-ray source may be positioned irrespective of the virtual image plane. By orientating the 3D CT image in different positions 21, 22 relative to the virtual X-ray source 24 and the virtual image plane 23 simulated X-ray images with the patient in these orientations are easily generated. This is exemplified here with the head tilted slightly 201, 202 with respect to the viewpoint and the virtual image plane. This is especially relevant for obtaining X-ray images acquired at slightly different orientations of the patient, a feature that is not easily feasible with actual X-ray images. For example, a surgeon may need an X-ray image from a very specific angle. But it may be impossible to predict this angle, the position of the bones may vary from patient to patient and dislocations of certain bones may be present. It may therefore be impossible to predict the optimal angle in order to avoid, or minimize, shadowing from various bones. The surgeon may consequently send the patient to an X-ray facility for obtaining a series of actual X-ray images in order to evaluate from where an optimal image should be obtained. This is followed by that the patient is resent to the X-ray facility for obtaining the optimal images. This is a slow and relatively expensive task, which furthermore unnecessarily exposes the patient to additional radiation. The present invention allows the surgeon, on the background of the CT scanning, to generate a series of simulated X-ray images and immediately choose the image that is obtained from the optimal viewpoint. This is fast and does not expose the patient to additional radiation.

The X-ray images are simulated from Computed Tomography by simulation algorithms that are texture based and adapted with special accumulation, color, and opacity buffers in a manner that Beer's law is approximated regarding the transmission and scattering of photons through physical media.

According to Beer's law, the intensity of an X-ray traversing through a material is attenuated in the following way:

$$I = I_{initial} * \mathrm{Exp}(-m*L) \quad (i)$$

where $I_{initial}$ is the initial intensity of the X-ray, m is the materials linear attenuation coefficient, and L is the thickness of the material.

As the linear attenuation coefficient depends on the material, the intensity of an X-ray passing though an object consisting of multiple materials is:

$$I = I_{initial} * \mathrm{Exp}(\int -m(x)dx) \quad (ii)$$

where m(x) is a function that maps a position, x, along the ray to the linear attenuation coefficient of the material at the point x of the ray. The function m(x) is integrated from a start position at the point source to an end position at the virtual image plane The result of a CT scan is a discrete 3D function that maps spatial locations to Hounsfield units. Hounsfield units are a standardized and accepted unit for reporting and displaying reconstructed X-ray CT values. The system of units represents a line transformation from the original linear attenuation coefficient measurements into one where water is assigned a value of zero and air is assigned a value of −1000. If $\mu w$, $\mu a$, and $\mu$ are the respective linear attenuation coefficients of water, air and a substance of interest, the Hounsfield value of the substance of interest is: $H=1000\,(\mu-\mu w)/(\mu w-\mu a)$. Thus, a change of one Hounsfield unit corresponds to 0.1% of the attenuation coefficient difference between water and air, or approximately 0.1% of the attenuation coefficient of water since the attenuation coefficient of air is nearly zero. The use of this standardized scale facilitates the intercomparison of CT values obtained from different CT scanners and with different X-ray beam energy spectra, although the Hounsfield value of materials whose atomic composition is very different from that of water will be energy dependent. By using exact values for relating Hounsfield units to attenuating values based on photon energy ensures that high-frequency information is included in the final simulated X-ray images.

The 3D function may now be used to simulate X-ray images of the same object in the following way: First the scanned 3D volume is mapped from Hounsfield units back to linear attenuation coefficients. A simulated X-ray image may consequently be generated by casting rays through the scanned 3D volume, and integrating (ii) along the path of each casted ray to calculate the intensity of the X-ray according to Beer's law.

Having estimated the intensity of the X-ray, it is possible to generate an image by mapping the X-ray intensities to color/gray scale values.

Figure 3:
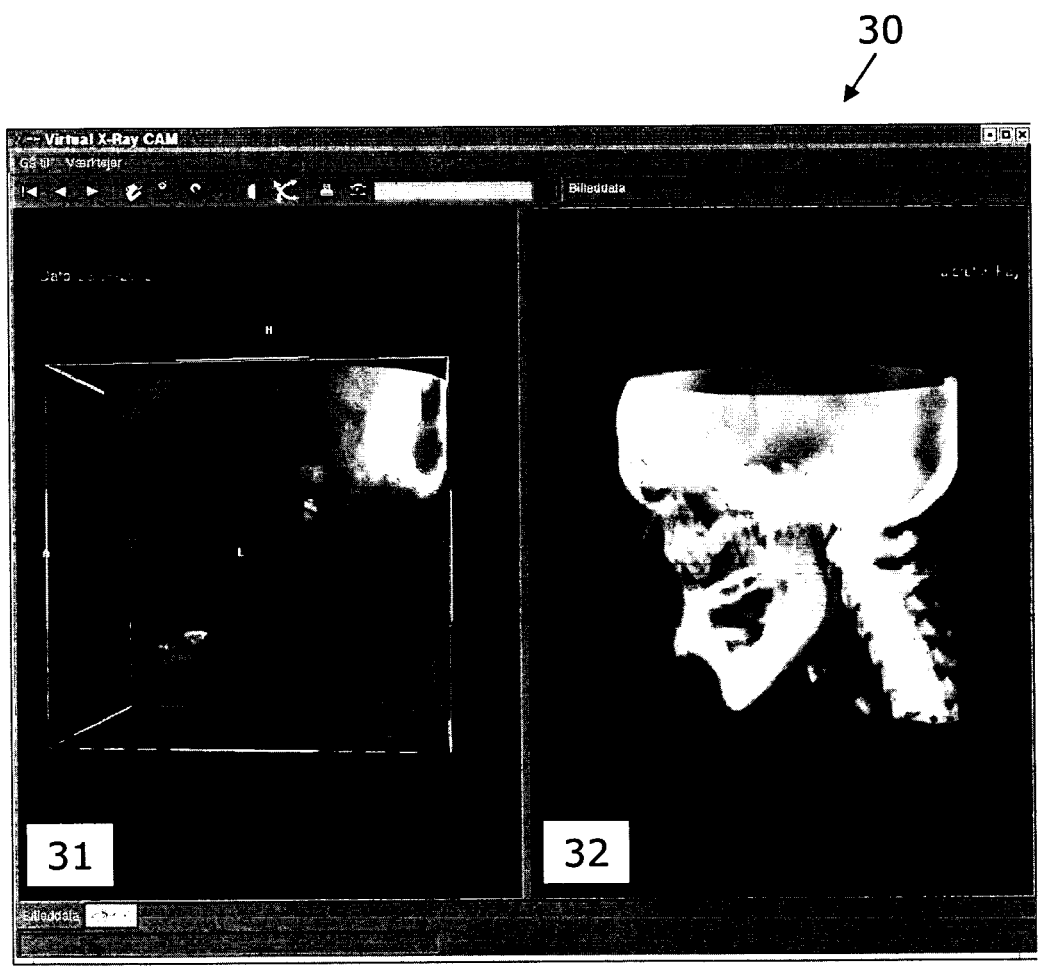
FIG. 3 shows a screenshot of a CT object and the corresponding simulated X-ray image obtained in connection with a preferred embodiment.
Figure 4:
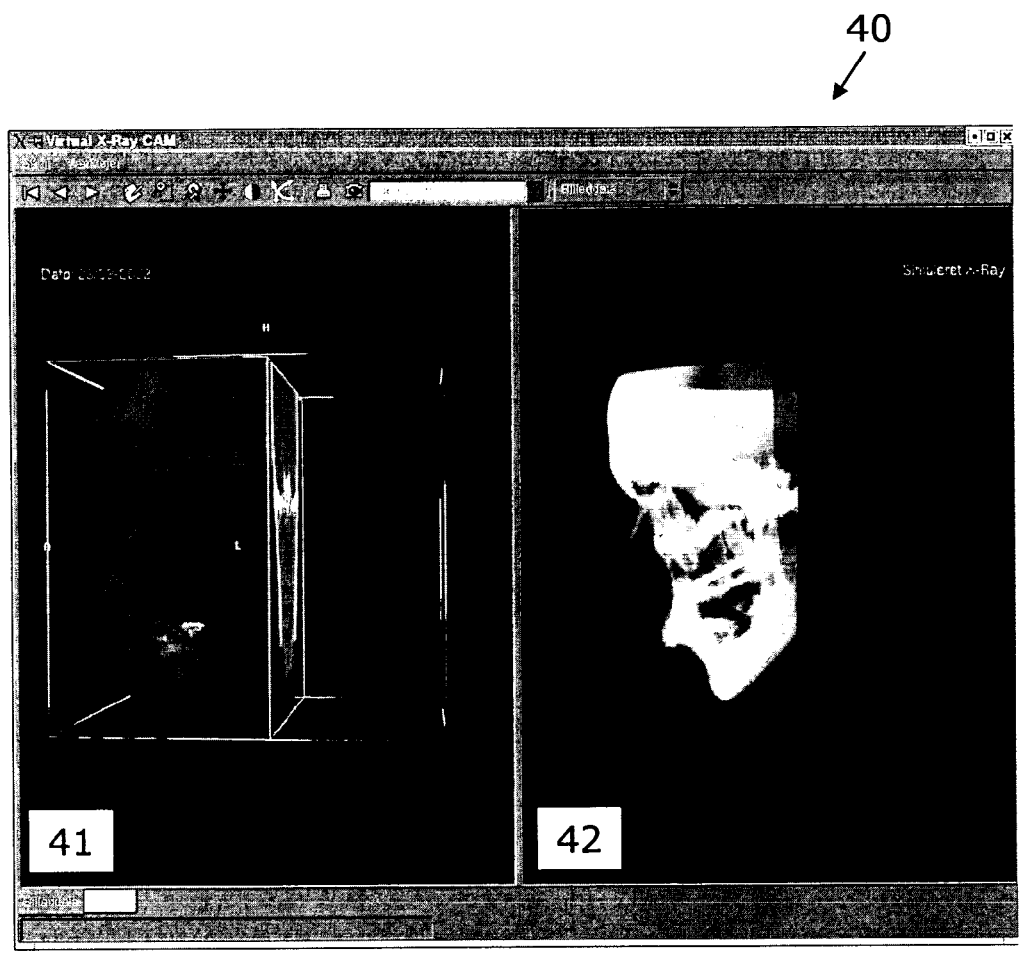
FIG. 4 shows another screenshot.

The 2D X-ray image may be simulated from any viewpoint. Two screenshots are presented in FIG. 3 and FIG. 4. In the screenshot 30 in FIG. 3 a 3D reconstruction of a patient's head is shown in the left half 31, and in the right half 32 is the corresponding simulated X-ray image shown. The X-ray image is simulated with respect to an image plane coincident with the image plane of the screenshot. It is possible to generate images from a viewpoint from which it is not possible to generate an actual X-ray image since the CT image may be orientated in any orientation (not shown) with respect to the virtual image plane. Many viewpoints exist which are not accessible in an actual X-ray apparatus. The viewpoint may even be moved within the CT object, so that only the tissue between the viewpoint and the virtual image plane contributes to the resulting simulated X-ray image. This may be advantageous, e.g. in the case where an image of a feature may not be obtained because another feature is shadowing and thereby blocking for the imaging of the feature of interest. In a similar manner may a part of the CT image be removed, in this way the removed part will not contribute in the simulation of the X-ray image. This is illustrated in FIG. 4, which is a screenshot 40 identical to the screenshot 30 in FIG. 3, except that a certain part of the CT object has been removed in the left half 41, and that this part does not appear in the simulated X-ray image in the right half 42 of the screenshot.

Figure 5:
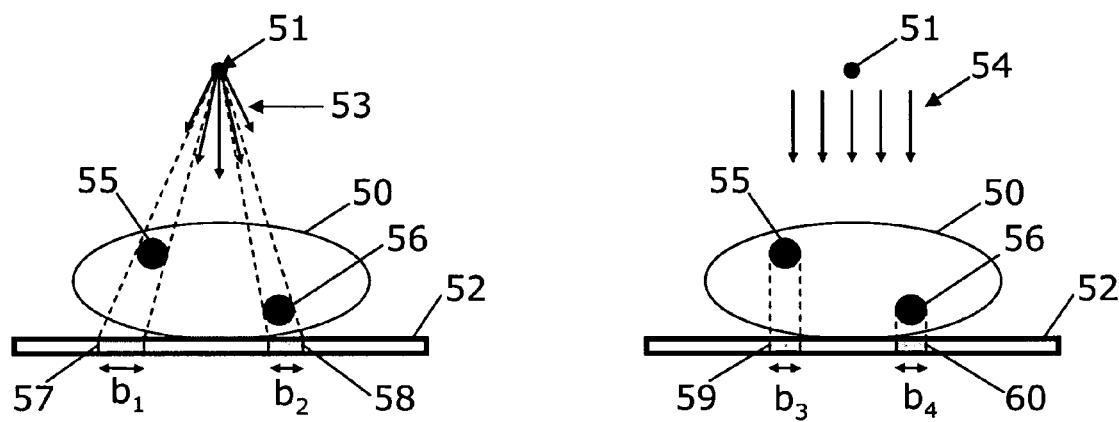
FIG. 5 illustrates the difference between simulating an ideal X-ray image versus simulating an actual X-ray image.

In FIG. 5 the simulation of an ideal X-ray image versus simulating an actual X-ray image is illustrated. A CT object 50 is positioned relative to a virtual X-ray source 51 and a virtual image plane 52. The X-ray image is simulated either by using divergent X-rays 53, or by using parallel propagating X-rays 54. The CT object contains a multitude of features 55, 56, features that will be visible in the simulated image. The features are, in this example, identical except that one of the features 55 is positioned further away from the virtual image plane 52, than the other feature 56.

In the case that divergent X-rays are used, the simulated X-ray image is distorted due to parallax. Objects are broadened and moved according to their position above the image plane, the higher above the image plane they are positioned, the more the feature is broadened and the further the feature is moved. Thus, feature one 55 is imaged with a width $b_1$ 57 larger than the width $b_2$ 58 of feature two 56, even though the features are identical.

In the case that parallel X-rays are used, the simulated X-ray image is not distorted due to parallax. In this case feature one 55 is imaged with a width $b_3$ 59 equal to the width $b_4$ 60.

Actual X-ray images obtained at an X-ray facility are always parallax distorted. It may therefore not always be possible to determine whether a feature is broad due to the position of the feature, or due to parallax distortion. One way to resolve this problem is to obtain X-ray images from another angle, but this requires resending the patient to the X-ray facility. This is expensive, takes time and re-exposes the patient to radiation. The present invention provides the possibility to generate an image with and without parallax distortion and thereby immediately to determine whether or not the width of an object of the X-ray image is largely affected by parallax distortion.

Although the present invention has been described in connection with preferred embodiments, it is not intended to be limited to the specific form set forth herein. Rather, the scope of the present invention is limited only by the accompanying claims.

The invention claimed is:

1. A method of generating a simulated 2D X-ray image from CT data of a patient's anatomy, said method comprising the steps of:

CT scanning the patient to generate corresponding CT data at a first time instance;

storing the CT data in a data repository;

retrieving the CT data at a second time instance after the first time instance;

generating a 3D CT image of the anatomy from the CT data; and positioning a virtual X-ray source relative to a virtual image plane to generate a corresponding 2D simulated X-ray image, being generated from an unrestricted viewpoint, wherein simulation algorithms are texture based and adapted with accumulation, color, and opacity buffers in such a manner that Beer's law is approximated regarding transmission and scattering of photons through physical media.

2. A method according claim 1, wherein the corresponding 2D simulated X-ray image is simulated using parallel propagating X-rays, so that the corresponding 2D simulated X-ray image is simulated free of parallax distortion.

3. A method according to claim 1, wherein the corresponding 2D simulated X-ray image is simulated using divergent X-rays, so that the corresponding 2D simulated X-ray image is simulated with parallax distortion as in actual X-ray images.

4. A method according to claim 1, wherein the CT data of patient anatomy is based on data which conforms to a DICOM standard implemented on PACS systems.

5. A computer readable medium encoded with a computer program adapted to perform the method of claim 1, when said program is run on a computer system.

6. A system for generating a simulated 2D X-ray image from CT data of a patient's anatomy, said system comprising:

a first device and at least second device, where the first device and at least second device are interconnected in a computer network;

where the first device stores CT data of the patient's anatomy; and where the at least second device includes a visualization device and an inputting device capable of accepting request actions;

wherein the patient CT data is accessed from the at least second device, so that a 3D CT image of a patient, and subsequently the simulated 2D X-ray image is visualized on the visualization device included in the at least second device, and simulation algorithms a processing device that processes which are texture based and adapted with accumulation, color, and opacity buffers in such a manner that Beer's law is approximated regarding transmission and scattering of photons through physical media.

* * * * *